United States Patent [19]
Hanson et al.

[11] Patent Number: 5,986,095
[45] Date of Patent: Nov. 16, 1999

[54] ENANTIOSELECTIVE PREPARATION OF HALOPHENYL ALCOHOLS AND ACYLATES

[75] Inventors: Ronald L. Hanson, Morris Plains; Ramesh N. Patel, Bridgewater; Laszlo J. Szarka, East Brunswick, all of N.J.

[73] Assignee: E.R. Squibb & Sons, Inc., Princeton, N.J.

[21] Appl. No.: 07/817,232

[22] Filed: Jan. 6, 1992

[51] Int. Cl.$^6$ .................................................. C07D 403/04
[52] U.S. Cl. ..................... 544/295; 544/334; 544/335; 544/398; 544/399; 560/106; 560/121; 560/122; 560/123; 560/124; 560/254; 568/807; 568/810; 568/812; 435/42; 435/118; 435/122; 435/135; 435/156
[58] Field of Search ..................... 544/334, 335, 544/398, 295, 399; 560/106, 129, 121, 123, 124, 122, 254; 568/807, 810, 812; 435/42, 118, 122, 135, 156

[56] References Cited

U.S. PATENT DOCUMENTS

| | | | |
|---|---|---|---|
| 3,684,477 | 8/1972 | Blumbergs et al. | 71/67 |
| 4,897,490 | 1/1990 | Sit et al. | 548/253 |

FOREIGN PATENT DOCUMENTS

| | | |
|---|---|---|
| 0257716 | 8/1987 | European Pat. Off. . |
| 0266217 | 5/1988 | European Pat. Off. . |
| 0328125 | 8/1989 | European Pat. Off. . |
| 337920 | 10/1989 | European Pat. Off. . |
| 357009 | 2/1990 | European Pat. Off. . |
| 0421636 | 9/1990 | European Pat. Off. . |
| 2224733 | 5/1990 | United Kingdom . |

OTHER PUBLICATIONS

March, J., Advanced Organic Chemistry, John Wiley and Sons, New York, 1985, pp. 334–336.
V. C. J. Sih et al., Angew. Chem., 96, 556–565, 1984.
M. J. Barton et al., Enzyme Microb. Technol., 12, 577–583, 1990.
T. R. Nieduzak et al., Tetrahedron: Asymmetry, vol. 2 113–122, 1991.
K. Laumen et al., J. Chem. Soc., Chem. Commun., 598–600, 1988.
C. J. Sih et al., Jounral of Industrial Microbiology, Suppl. No. 3, 221–229, 1988.
B. Cambou et al., J. Am. Chem. Soc., 106, 2687–2692, 1984.
S. Hsu et al., Tetrahedron Letters, vol. 31, No. 44, 6403–6406, 1990.
K. A. Babiak et al., J. Org. Chem., 55, 3377–3381, 1990.
M. Inagaki et al., Bull. Inst. Chem. Res., vol. 67, No. 3, 1989.
C. G. Rabiller et al., Tetrahedron, 46 (12), 4231–40, 1990.
K. Nakamura et al., Agric. Biol. Chem., 54 (6), 1569–1570 (1990).
H. Hirata et al., J. Biotechnol., 14 (2), 156–167 (1990).
Peri et al., J. Am. Chem. Soc., 112 (5), 1897–1905 (1990).
A. Scilimati, et al., Tetrahedron Lett., 29 (39), 4927–4930 (1990).
C. Feichter et al., Tetrahedron Lett., 30 (5), 551–552 (1989).
J. Hiratake et al., J. Org. Chem., 52 (26), 6130–6133 (1988).
B. Cambou et al., Biotechnol. Bioeng., 26 (12), 1449–1454 (1984).
Derwent Abstract No. 90–032935/05, 1989.
Derwent Abstract No. 90–258265/34, 1990.

*Primary Examiner*—Richard L. Raymond

[57] ABSTRACT

A process is described for preparing a compound of the formula

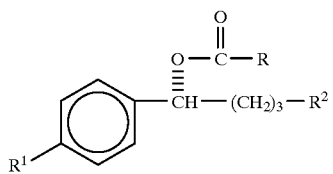

or the S-enantiomer thereof,
wherein:
  R is alkyl, aryl, cycloalkyl, aralkyl, or cycloalkylalkyl,
  $R^1$ is halogen;
  $R^2$ is halogen, alkyl, cycloalkyl, aryl or

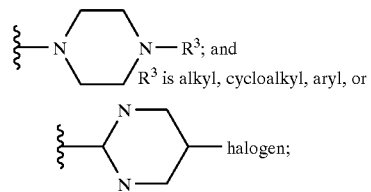

wherein the process comprises treating the associated racemic alcohol with an acylating agent

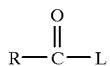

(wherein L is a leaving group) and an enzyme or microorganism capable of enantioselective acylation. This process may also be used to isolate the unreacted R- or S-alcohol. The acylated product may be enantioselectively hydrolyzed with a lipase or lipase-supplying microorganism to the S- or R-alcohol. Compounds prepared by this invention are useful antipsychotic agents or useful intermediates therefor.

16 Claims, No Drawings

ENANTIOSELECTIVE PREPARATION OF HALOPHENYL ALCOHOLS AND ACYLATES

FIELD OF INVENTION

This invention relates to preparation of antipsychotic agents and chemical intermediates, particularly BMY 14,802 and its intermediates.

BACKGROUND OF THE INVENTION

Antipsychotic agents are described in U.S. Pat. Nos. 4,605,655 and 4,994,460, issued Aug. 12, 1986 and Feb. 19, 1991, respectively. Of these agents, a compound identified as BMY 14,802 having the structure

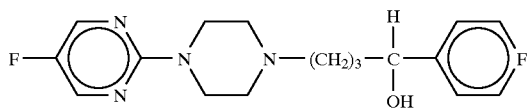

is preferred. The R(+) isomer of BMY 14,802 and the other compounds disclosed in these patents are more active. No enzymatic or microbial preparations of these compounds is known, and chemical selective preparation is difficult. A need exists, therefore, for an enantioselective preparation of these compounds in high yield and high stereoisomeric purity.

BRIEF DESCRIPTION OF INVENTION

In accordance with the present invention, a substrate of the formula

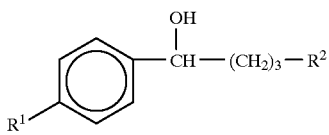

I is selectively acylated to a compound of the formula

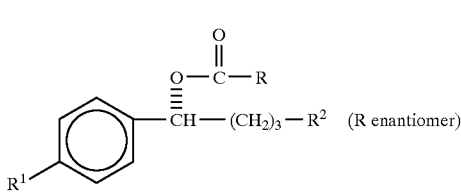

IIA or a compound of the formula

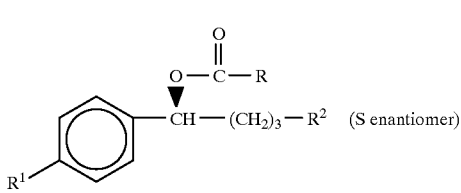

IIB by treatment with an acylating agent

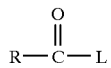

III and an enzyme or microorganism capable of enantioselective acylation of alcohols in an organic solvent, after which the selected acylate compound IIA or IIB is recovered therefrom.

Also in accordance with the present invention, compound IIA, IIB or the associated racemate is selectively hydrolyzed by treatment with water and a lipase or a lipase-supplying microorganism in the presence of an organic solvent to form

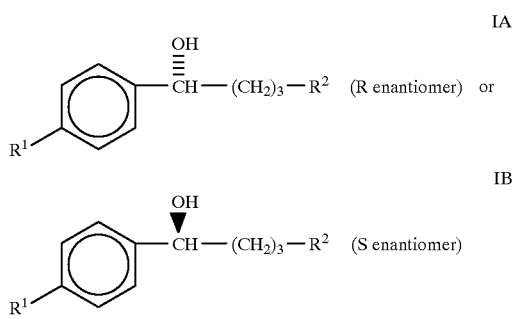

Further in accordance with the present invention, compound I may be acylated and hydrolyzed as described above to form compound IA or IB. In this combined process, the enzyme or microorganism for the acylation and hydrolysis step may be the same.

Further still in accordance with the present invention, the selective acylation of compound I may be used for enantioselective preparation of compound IA or IB, in which racemate I is treated with an acylating agent and enzyme or microorganism as described above, after which the unreacted alcohol IA or IB is recovered therefrom.

In compounds I through III and throughout this specification, the symbols are defined as follows:

R is alkyl, aryl, cycloalkyl, aralkyl, or cycloalkylalkyl;

L is a leaving group;

$R^1$ is halogen (fluorine preferred), $R^2$ is halogen (chlorine preferred), alkyl, cycloalkyl, aryl or

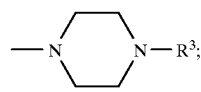

and $R^3$ is alkyl, cycloalkyl, aryl or

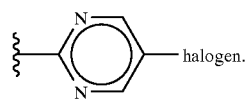

The following moieties are preferred for the process of this invention:

R is methyl;
R¹ is fluorine; and
R² is chlorine or

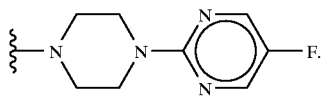

Compounds I to III are useful, inter alia, as antipsychotic agents or intermediates in the preparation thereof. See U.S. Pat. Nos. 4,605,655 and 4,994,460. Intermediates produced by the processes of this invention may be used in procedures described in the cited patents to prepare useful antipsychotic agents. S enantiomers prepared by processes of this invention may also be inverted to the associated R enantiomers. See, for example, Mitsunobu reaction procedures described in Babiak et al., *J. Org. Chem.* 55, 3377–3378 (1990).

The processes of the present invention have the advantage of producing an enantiospecific result. When the transformation is catalyzed at ambient temperature and pressure, one obtains high conversion and enantiomeric purity of the desired enantiomer.

DETAILED DESCRIPTION OF THE INVENTION

The following definitions apply throughout this specification, unless otherwise limited in specific instances. These definitions apply to the terms as used individually or as part of a larger group.

The terms "alkyl" and "alkenyl" refer to straight and branched chain hydrocarbon groups having 1 to 10 carbon atoms.

The term "cycloalkyl" refers to groups having 3, 4, 5, 6 or 7 carbon atoms.

The term "aryl" refers to phenyl and substituted phenyl. Exemplary substituted phenyl groups are substituted with 1, 2 or 3 amino (—NH₂), alkylamino, dialkylamino, nitro, halogen, hydroxyl, trifluoromethyl, alkyl (of 1 to 4 carbon atoms), alkoxy (of 1 to 4 carbon atoms), alkanoyloxy, carbamoyl or carboxyl groups.

The term "halogen" refers to fluorine, chlorine, bromine and iodine.

"Fermentation" as used herein refers to growth of the microbial cells to be used in a transformation process.

Typical organic solvents suitable for use in the present process include, but are not limited to, 1,1,2-trichloro-1,2, 2-trifluoroethane, toluene, cyclohexane, benzene, hexane, heptane, isooctane and octane. Heptane is preferred for acylation of compound I. Toluene is preferred for the hydrolysis of compound II wherein

The enzyme or microorganism used in the present process can be any enzyme or microorganism having the ability to catalyze the enantioselective esterification of alcohols I or hydrolysis of acylates II. Various enzymes, such as esterases and lipases, regardless of origin or purity, are suitable for use in the present invention. The enzyme can be in the form of a mixture of animal and plant enzyme, cells of microorganisms, crushed cells or extracts of cells.

Typical genuses of microorganism suitable as sources of catalyzing enzymes including Mucor, Rhizopus, Aspergillus, Candida, Pseudomonas, Chromobacterium, Penicillium, Chaetomium, Humicola, Geotrichum, Kibdelosporangium, and the like.

Commercially available enzymes suitable for use in the present invention include lipases, such as Amano PS 30 (Pseudomonas) which is preferred for the acylation and hydrolysis wherein R¹ is fluoro and R² is chloro; Amano AY-30 (*Candida cylindracea*); Amano N (*Rhizopus niveus*); Amano R (Penicillium sp.); Amano FAP (*Rhizopus oryzae*); Amano AP-12 (*Aspergillus niger*); Amano MAP (*Mucor meihei*); Amano GC-20 (*Geotrichum candidum*) which is preferred for the acylation and hydrolysis wherein R¹ is fluoro and R² is

Biocatalysts *Geotrichum candidum*; Biocatalysts *Aspergillus niger*; Biocatalysts *Candida cylindracea*; Sigma L-0382 (porcine pancreas); Sigma L-3001 (Wheat germ); Sigma L-1754 (*Candida cylindracea*); Sigma L-0763 (*Chromobacterium viscosum*); Mieto-Sangkyo OF (*Candida rugosa*); and Amano K-30 (*Aspergillus niger*). Additionally, enzymes derived from animal tissue include esterase from pig liver, α-chymotrypsin and pancreatin from pancreas.

Specific microorganisms suitable for use in the present process include *Pseudomonas fluorescens, Pseudomonas putida, Pseudomonas ovalis, Aspergillus niger, Rhizopus oryzae, Candida cylindracea, Candida rugosa, Rhizopus niveus, Penicillium, Mucor meihei, Geotrichum candidum, Chromobacterium viscosum, Kibdelosporangium aridum* and the like.

Microbially derived enzymes may be used in free state or immobilized on support. Suitable carriers are diatomaceous earth (porous Celite® Hyflo Supercel), microporous polypropylene (Enka Accurel® polypropylene powder), or a nonionic polymeric adsorbent such as Amberlite® XAD-2 (polystyrene), XAD-7 (polyacrylate) and the like. A carrier immobilizes the enzyme, which controls the enzyme particle size and prevents aggregation of the enzyme particles when used in an organic solvent. This can be accomplished, for example, by precipitating an aqueous solution of the enzyme with cold acetone in the presence of the Celite Hyflo Supercel followed by vacuum drying, or in the case of a nonionic polymeric absorbent, incubating enzyme solutions with absorbent on a shaker, removing excess solution and drying enzyme-adsorbent resins under vacuum.

Desired enantiomers can be isolated from the reaction mixture and purified by known methodologies such as extraction, distillation, crystallization, column chromatography, and the like.

As will be apparent to those skilled in the art, the process of the present invention can be carried out using microbial cells containing an appropriate enzyme. When using a microorganism to perform the resolution, the present process is conveniently carried out by adding the cells and the racemic starting materials to the desired solution. Cells may be used in the form of intact cells, dried cells such as lyophilized, spray-dried or heat-dried cells, immobilized cells, or cells treated with organic solvents such as acetone or toluene. Cells may also be used in the form of treated cell material such as ruptured cells or cell extract. Cell extracts immobilized on Celite® or Accurel® polypropylene as described earlier can also be used.

Appropriate media for growing microorganisms for this process typically include necessary carbon sources, nitrogen sources, and trace elements. Inducers such as fats or oils may also be added.

Carbon sources include sugars such as maltose, lactose, glucose, fructose, glycerol, sorbitol, sucrose, starch, mannitol, propylene glycol, and the like; organic acids such as sodium acetate, sodium citrate, and the like; amino acids such as sodium glutamate and the like; alcohols such as ethanol, propanol, and the like; and oils such as soybean oil and the like.

Nitrogen sources include N-Z amine A, corn steep liquor, soy bean meal, beef extracts, yeast extracts, baker's yeast, tryptone, nutrisoy, peptone, yeastamin, sodium nitrate, ammonium sulfate, and the like.

Trace elements include phosphates and magnesium, manganese, calcium, cobalt, nickel, iron, sodium, and potassium salts.

It is within the scope of this invention that appropriate media may include more than one carbon or nitrogen source and may include a mixture of several.

A typical medium for growth of such cells is:

| Material Name | Concentration (% w/v) |
| --- | --- |
| Cerelose hydrate | 4.4 |
| Ammonium sulfate | 0.75 |
| Yeast extract | 0.10 |
| Uncon antifoam | 0.04 |
| Corn steep liquid | 3.3 |

The pH of the medium is adjusted to 6.8 to 7.0 prior to sterilization.

The temperature of the reaction mixture should be maintained to ensure that there is sufficient energy available for the process. A suitable temperature range is about 15° C. to 60° C. A preferred temperature range is about 25° C. to 50° C.

The reaction time for the transformation process is about 45 to 250 hours, preferably 48 to 72 hours, measured from the time of initially treating the substrate with the enzyme or microorganism to achieve complete transformation.

Acylating agents useful in the present invention are organic acids, halides, esters, and acid anhydrides. Exemplary acylating agents are such as acetic acid, isopropenyl acetate, vinyl butyrate, vinyl acetate, various other acetates, and the like. Additional acylating agents are generally known in the art; see, for example, *Methoden der Organischen Chemie* (Houben-Weil), Vol. XV, part II, p. 1 et seq. (1974). Isopropenyl acetate, vinyl acetate, and vinyl butyrate are preferred. Suitable leaving groups L are hydroxy, alkoxy, phenoxy, benzyloxy, alkenyloxy and the like.

The following examples and preparations describe the manner and process of making and using the invention and are illustrative rather than limiting. These examples represent preferred embodiments, although other embodiments fall within the spirit and scope of the invention.

EXAMPLES 1 and 2

R(+)-α-(3-Chloropropyl)-4-fluorobenzene methanol, acetate ester

Example 1

Racemic α-(3-chloropropyl)-4-fluorobenzenemethanol (5 g) and isopropenyl acetate (5 g) were dissolved in 50 mL of heptane. 7 mL of this solution was added to 2 g of each lipase listed in Table 1, and the suspension was shaken at 25° C., 250 rpm. Samples were removed at intervals and resolved into R and S alcohols using a Chiralcel OB 25×0.46 cm column. The mobile phase was 94% hexane, 6% isopropanol. Temperature was 25° C. (ambient), detection wavelength was 270 nm and flow rate was 1 mL/min. R and S alcohols were resolved and separated from the acetate by this column, but racemic acetate was not resolved. Acetate optical purity was determined with a Chiralcel OK column. The R alcohol was preferentially acetylated by each of four lipases in Table 1, but Amano lipase PS30 gave the fastest conversion and highest optical purity of products.

Example 2

Racemic α-3-chloropropyl-4-fluorobenzenemethanol (100 g), distilled isopropenyl acetate (100 g), Amano lipase PS30 (200 g) and heptane (1 L) were shaken at 25° C., 250 rpm. After 55 hours, the enzyme was removed by filtration and washed three times with 150 mL of heptane. The combined heptane solutions contains the S alcohol (53.9 g, 90.3% optical purity) and the R acetate (56.4 g, 94.0% optical purity).

The filtered enzyme was reused in the same procedure to give, after 63 hours, 45.4 g of the S alcohol (100% optical purity) and 67.0 g of the R acetate (87.9% optical purity).

EXAMPLES 3 and 4

R(+)-α-(3-Chloropropyl)-4-fluorobenzenemethanol

Example 3

Racemic α-(3-chloropropyl)-4-fluorobenzenemethanol, acetate ester (1 g), calcium carbonate (0.5 g), Amano PS30 lipase immobilized on Accurel PP (1 g), water (1 mL), and heptane (10 mL) were shaken at 40° C., 250 rpm. After 162 hours, 39% of the acetate had been hydrolyzed to give the R alcohol (95.4% optical purity).

Example 4

The R acetate prepared as described in Example 2 (0.5 g), Amano PS30 lipase immobilized on Accurel PP (0.5 g), calcium carbonate (0.5 g), water (1 mL) and heptane (10 mL) were shaken at 40° C., 250 rpm. After 246 hours, 69% of the acetate had been hydrolyzed to the desired R alcohol (100% optical purity).

EXAMPLES 5 and 6

R(+)-1-(4-Fluorophenyl)-4-[4-(5-fluoro-2-pyrimidinyl)-1-piperazinyl]-1-butanol (BMY 14, 802)

Example 5

50 mg of BMY 14802 acetate-hydrochloric acid, 4 mL of water, 0.5 mL of 1 M potassium phosphate pH 7.4, 0.5 mL of toluene, and 100 mg of enzyme were shaken at 25° C., 200 rpm for the indicated time. 5 mL of 1 M potassium phosphate pH 8 and 10 mL of ethyl acetate were added for extraction. BMY 14802 and BMY 14802 acetate in the ethyl acetate extract were measured by GC using an HP ultra 2 column with injector temperature 230° C., column temperature 245° C., and FID detector temperature 270° C. Optical purity of BMY 14802 was determined by HPLC using a Chiralcel OD column. The results for 5 lipases are shown in Table 2.

Example 6

200 mg of BMY 14802 acetate.hydrochloric acid, 1 mL of 1 M potassium phosphate pH 7.4, 17 mL water and 2 mL toluene were brought to pH 7 with 1 N sodium hydroxide. 400 mg Amano lipase GC-20 was added and the reaction was maintained at 25° C. and pH 7 with 1 N sodium hydroxide. After 69 hours, the pH was raised to 8 with 5 N sodium hydroxide and 20 mL ethyl acetate was added for extraction. The R enantiomer of BMY 14802 was obtained in 47.6% yield with 97.9% optical purity.

TABLE 1

Acetylation of Racemic α-(β-chloropropyl)-4-fluorobenzenemethanol

| Lipase | Source | Time (hours) | Conversion % | Alcohol % S | Acetate % R |
|---|---|---|---|---|---|
| Amano PS30 | Amano (Pseudomonas) | 48 | 45.6 | 87.4 | 89.7 |
|  |  | 72 | 51.5 | 100.0 | 89.0 |
| GC-20 | Amano (Geotrichum candidum) | 48 | 6.4 | 53.2 | 63.6 |
|  |  | 72 | 8.5 | 53.6 | 70.6 |
| Geotrichum candidum | Biocatalysts | 48 | 2.8 | 52.3 | 60.0 |
|  |  | 72 | 7.8 | 53.4 | 71.5 |
| AY-30 | Amano (Candida species) | 48 | 6.4 | 53.7 | 75.3 |
|  |  | 72 | 9.8 | 54.7 | 69.2 |

TABLE 2

Hydrolysis of BMY 14802 Acetate

| Enzyme | Time (Hours) | Amount (mg) | Source | Conversion % | Optical Purity |
|---|---|---|---|---|---|
| GC-20 | 89 | 100 | Amano (Geotrichum candidum) | 31.0 | 96.3 |
| Aspergillus niger | 89 | 200 | Biocatalysts | 28.6 | 16.7 |
| Candida cylindracea | 89 | 200 | Biocatalysts | 33.2 | 94.9 |
| OF | 89 | 100 | Mieto - Sangkyo (Candida rugosa) | 13.4 | 98.0 |
| AY-30 | 89 | 100 | Amano (Candida species) | 43.6 | 83.5 |

What is claimed is:

1. A process for selectively preparing an R-enantiomer of the formula

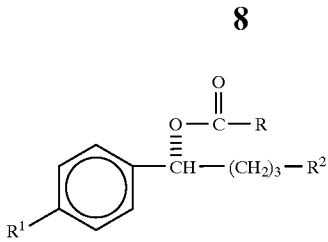

wherein:
R is alkyl, aryl, cycloalkyl, aralkyl, or cycloalkylalkyl;
$R^1$ is halogen;
$R^2$ is halogen, alkyl, cycloalkyl, aryl or

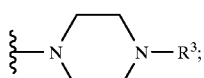

and
$R^3$ is alkyl, cycloalkyl, aryl, or

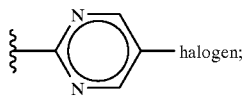

and wherein the process comprises:
(a) treating a substrate of the formula

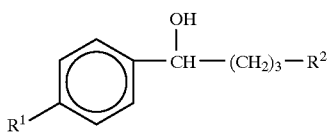

with
(i) an acylating agent

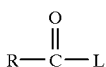

wherein L is a leaving group and
(ii) a microorganism selected from Mucor, Rhizopus, Aspergillus, Pseudomonas, Chromobacterium, Penicillium, Chaetomium, Humicola, Geotrichum, and Kibdelosporangium or an enzyme derived therefrom; and
(b) recovering the acylated product therefrom.

2. A process for selectively preparing an R-enantiomer of the formula

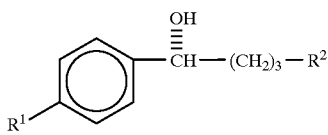

wherein:
R is alkyl, aryl, cycloalkyl, aralkyl, or cycloalkylalkyl;
$R^1$ is halogen;

$R^2$ is halogen, alkyl, cycloalkyl, aryl

and $R^3$ is alkyl, cycloalkyl, aryl, or

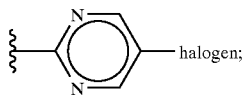

and wherein the process comprises:
(a) hydrolyzing a compound of the formula

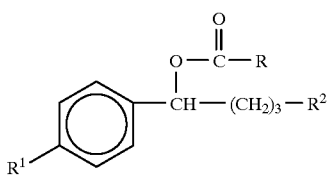

in racemic form, or the R- enantiomer thereof, by treatment with water and a lipase-supplying microorganism selected from Mucor, Rhizopus, Aspergillus, Pseudomonas, Chromobacterium, Penicillium, Chaetomium, Humicola, Geotrichum, and Kibdelosporangium or a lipase derived therefrom in the presence of an organic solvent; and
(b) recovering the product therefrom.

3. A process for preparing an R-enantiomer of the formula

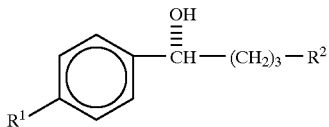

wherein:
R is alkyl, aryl, cycloalkyl, aralkyl, or cycloalkylalkyl;
$R^1$ is halogen;
$R^2$ is halogen, alkyl, cycloalkyl, aryl or

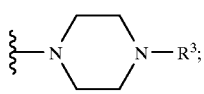

and
$R^3$ is alkyl, cycloalkyl, aryl, or

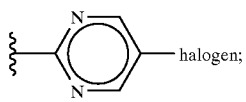

and wherein the process comprises:

(a) treating a substrate of the formula

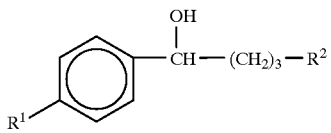

with
(i) an acylating agent

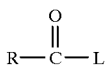

wherein L is a leaving group in an organic solvent; and
(ii) A microorganism selected from Mucor, Rhizopus, Aspergillus, Pseudomonas, Chromobacterium, Penicillium, Chaetomium, Humicola, Geotrichum, and Kibdelosporangium or an enzyme derived therefrom; and
(b) recovering the acylate product of step (a);
(c) hydrolyzing the recovered acylate product of step (a) with water and a lipase or lipase-supplying microorganism in the presence of an organic solvent; and
(d) recovering the hydrolyzed product of step (c).

4. A process for preparing

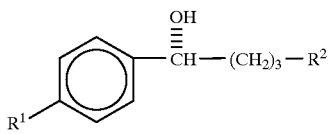

an S-enantiomer of the formula

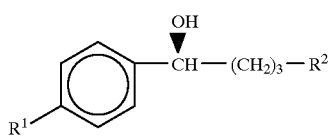

wherein:
R is alkyl, aryl, cycloalkyl, aralkyl, or cycloalkylalkyl;
$R^1$ is halogen;
$R^2$ is halogen, alkyl, cycloalkyl, aryl, or

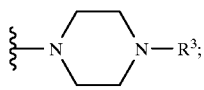

and
$R^3$ is alkyl, cycloalkyl, aryl, or

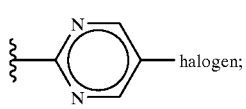

and wherein the process comprises:

(a) treating a substrate of the formula

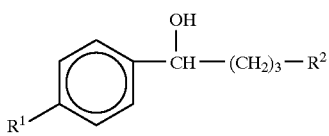

with (i) an acylating agent

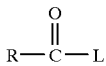

wherein L is a leaving group; and (ii) a microorganism selected from Mucor, Rhizopus, Aspergillus, Pseudomonas, Chromobacterium, Penicillium, Chaetomium, Humicola, Geotrichum, and Kibdelosporangium or an enzyme derived therefrom; and (b) recovering the unreacted alcohol product therefrom.

5. The process of any of claims 1 to 4, wherein R is alkyl.

6. The process of any of claims 1 to 4, wherein R is methyl.

7. The process of claims 1, 3 or 4, wherein the acylating agent is selected from isopropenyl acetate, vinyl acetate, and vinyl butyrate.

8. The process of any of claims 1 to 4, wherein $R^2$ is chlorine or

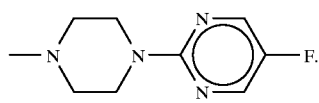

9. The process of any of claims 1 to 4, wherein the substrate is treated with a microorganism selected from:

*Pseudomonas fluorescens, Pseudomonas putida, Pseudomonas ovalis, Escherichia coli, Aspergillus niger, Rhizopus oryzae Candida cylindracea, Rhizopus niveus, Penicillium, Mucor meihei, Geotrichum candidum, Chromobacterium viscosum* and *Kibdelosporangium aridum.*

10. The process of any of claims 1 to 4, wherein the substrate is treated with a selective lipase selected from Amano PS-30, Amano AY-30, Amano N, Amano R, Amano AP-12, Amano MAP, Amano GC20, Sigma L-0382, Sigma L-3001, Sigma L-1754, Sigma L-0763, Mieto-Sangkyo OF, Amano K-30, Biocatalysts *Geotrichum candidum*, Biocatalysts *Aspergillus niger*, and Biocatalysts *Candida cylindracea.*

11. The process of claim 1, further comprising hydrolyzing the product of claim 1 to form an R-enantiomer of the formula

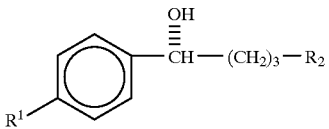

or an S-enantiomer of the formula

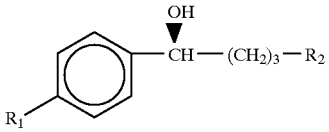

12. The process of of any claims 1 to 4, wherein $R^1$ is fluoro, $R^2$ is chloro, and the enzyme is Amano PS30.

13. The process of any of claims 1 to 4, wherein $R^1$ is fluoro $R^2$ is

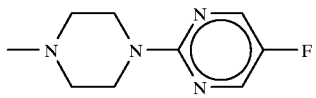

and the enzyme is Amano GC20.

14. The process of any of claims 1 to 4, wherein the microorganism is selected from Pseudomonas, Geotrichum, Candida, and Aspergillus.

15. A process for selectively preparing an R-enantiomer of the formula

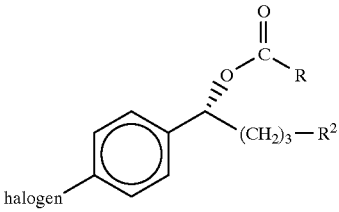

wherein:

R is alkyl, aryl, cydoalkyl, aralkyl, or cycloalkylalkyl;

$R^2$ is halogen, alkyl, cycloalkyl, aryl or

$R^3$ is alkyl, cycloalkyl, aryl, or

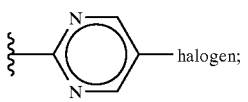

and wherein the process comprises:

(a) treating a substrate of the formula

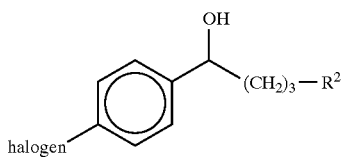

with
(i) an acylating agent of the formula

wherein L is a leaving group, and
(ii) a microorganism selected from the group consisting of Pseudomonas, Geotrichum, and Candida or an enzyme derived therefrom; and
(b) recovering the acylated product therefrom.

16. A process for selectively preparing an R-enantiomer of the formula

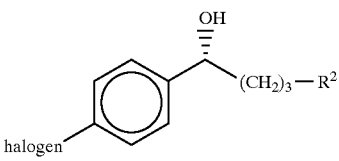

which comprises:

(a) hydrolyzing the product of claim 15 with water and a microorganism selected from the group consisting of Geotrichum, Candida, and Aspergillus or an enzyme derived therefrom in the presence of an organic solvent; and
(b) recovering the acylated product therefrom.

* * * * *